United States Patent [19]

Yamamoto et al.

[11] Patent Number: 5,605,973
[45] Date of Patent: Feb. 25, 1997

[54] BISAMIDRAZONE COMPOUND AND VULCANIZING AGENT FOR FLUORINE-CONTAINING ELASTOMER COMPRISING THE SAME

[75] Inventors: Yuichi Yamamoto; Satoru Saito; Haruyoshi Tatsu, all of Ibaraki, Japan; Lev S. German, deceased, late of Moscow, Russian Federation, by Elena N. German, heir; Ziefman Y. Vilovich, Moscow, Russian Federation; Postovoi S. Anatol'evich, Moscow, Russian Federation; Rusanov A. Lvovich, Moscow, Russian Federation

[73] Assignee: Nippon Mektron, Limited, Tokyo, Japan

[21] Appl. No.: 547,031

[22] Filed: Oct. 23, 1995

[30] Foreign Application Priority Data

Oct. 21, 1994 [JP] Japan ...................................... 6-282943

[51] Int. Cl.$^6$ ............................... C08L 27/12; C08K 5/29
[52] U.S. Cl. ...................... 525/326.3; 525/376; 564/226
[58] Field of Search ................... 525/326.3, 376; 564/226

[56] References Cited

U.S. PATENT DOCUMENTS 5,101,411  3/1992  Terao et al. ............................. 372/21

FOREIGN PATENT DOCUMENTS 0110420  12/1983  European Pat. Off. .
59-109546  6/1984  Japan .
2145095  10/1983  United Kingdom .

OTHER PUBLICATIONS

*Chemical Abstracts*, vol. 82, No. 11, 1975, Columbus, Ohio, U.S.; abstract No. 72892h.
*Chemical Abstracts*, vol. 87, No. 7, 1977, Columbus, Ohio, U.S.; abstract No. 52448t.
*J. Am. Chem. Soc.*, vol. 107, 1985 pp. 6970–6975, A. Streitwieser at al.
*Russian Chemical Reviews*, vol. 56, No. 3, 1987, pp. 288 – 298.
*Chemical Abstracts*, vol. 116, No. 18, 1992, Columbus, Ohio, U.S.; abstract No. 183382g.
*Chemical Abstracts*, vol. 112, No. 19, 1990, Columbus, Ohio, U.S.; abstract No. 178279 s.

*Primary Examiner*—David Buttner
*Attorney, Agent, or Firm*—Barnes & Thornburg

[57] ABSTRACT

Novel compound, 2,2-bis(4-carboxyphenyl)hexafluoropropane bisamidrazone, obtained by conversion of the carboxy groups of 2,2-bis(4-carboxyphenyl)hexafluoropropane to acid chloride groups, followed by reaction with ammonia; dehydration reaction of the resulting 2,2-bis(4-carboxyphenyl)hexafluoropropane diamide; reaction of the thus obtained 2,2-bis(4-cyanophenyl)hexafluoropropane with alcohol; and reaction of the resulting 2,2-bis(4-carboxyphenyl)hexafluoropropane bisiminoalkyl ether with hydrazine is a useful vulcanizing agent for fluorine-containing elastomer having cyano group.

2 Claims, No Drawings

BISAMIDRAZONE COMPOUND AND VULCANIZING AGENT FOR FLUORINE-CONTAINING ELASTOMER COMPRISING THE SAME

BACKGROUND OF THE INVENTION

1. Field of the Invention

The present invention relates to a bisamidrazone compound and a vulcanizing agent for fluorine-containing elastomer containing the same, and more particularly to a bisamidrazone compound as a novel compound and a vulcanizing agent for fluorine-containing elastomer having cyano groups as cross-linkable groups, which comprises the same.

2. Related Prior Art

JP-A-59-109546 discloses a fluorine-containing elastomer composition which comprises a terpolymer of tetrafluoroethylene, perfluoro(methyl vinyl ether) and cyano group-containing (perfluorovinylether) represented by the following general formula:

$$CF_2=CF[OCF_2CF(CF_3)]nO(CF_2)mCN$$

wherein n: 1~2 and m: 1~4
and a bis(aminophenyl) compound represented by the following general formula as a cross-linking agent:

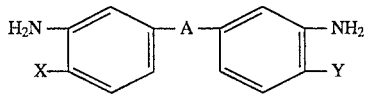

wherein A is an alkylidene group having 1 to 6 carbon atoms, a perfluoroalkylidene group having 1 to 10 carbon atoms, a $SO_2$ group, an O atom, a CO group or a carbon-carbon bond capable of directly bonding two benzene rings, and X and Y are hydroxyl groups or amino groups.

However, vulcanized products obtained by vulcanization of such a fluorine-containing elastomer composition are not satisfactory at all in the compression set.

SUMMARY OF THE INVENTION

An object of the present invention is to provide a novel bisamidrazone compound capable of producing vulcanization product having a satisfactory compression set, when used as a vulcanizing agent for fluorine-containing elastomer having cyano groups as cross-linkable groups.

Another object of the present invention is to provide a process for producing such a novel bisamidrazone compound.

Other object of the present invention is to provide a curable, fluorine-containing elastomer composition, which comprises a fluorine-containing elastomer having cyano groups as cross-linkable groups and a bisamidrazone compound.

DETAILED DESCRIPTION OF THE INVENTION

According to the present invention, there is provided a novel bisamidrazone compound represented by the following general formula [I]:

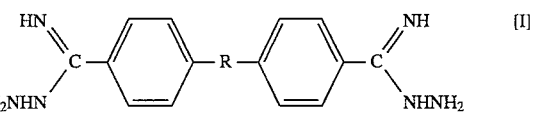

wherein R is an alkylidene group having 1 to 6 carbon atoms, preferably an isopropylidene group, or a perfluoroalkylidene group having 1 to 10 carbon atoms, preferably a perfluoroisopropylidene group, among which particularly preferable is a perfluoroisopropylidene group, where the resulting bisamidrazone compound is 2,2-bis(4-carboxyphenyl)hexafluoropropane bisamidrazone. A process for producing this compound through a series of the following steps will be described below:

(1) Two moles of toluene is made to react with one mole of perfluoroacetone $(CF_3)_2CO$ to obtain the following compound:

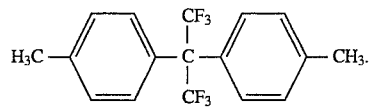

Then, the thus obtained compound is oxidized to obtain the following 2,2-bis(4-carboxyphenyl)hexafluoropropane:

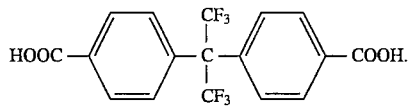

Then, the thus obtained compound is made to react with thionyl chloride $SO_2Cl$ in the presence of a pyridine catalyst to convert the carboxyl groups to an acid chloride groups, and further made to react with aqua ammonia to obtain the following 2,2-bis(4-carboxyphenyl)hexafluoropropane diamide:

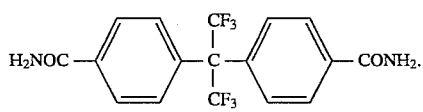

(2) The thus obtained 2,2-bis(4-carboxyphenyl)hexafluoropropane diamide is made to react with thionyl chloride in a solvent such as dehydrated dimethylformamide or the like to conduct a dehydration reaction, whereby 2,2-bis(4-cyanophenyl)hexafluoropropane having the following formula [II'] is obtained:

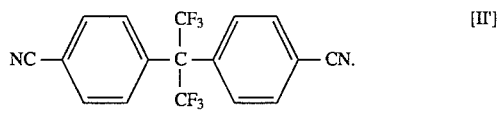

(3) The thus obtained 2,2-bis(4-cyanophenyl)hexafluoropropane is made to react with an alcohol such as methanol, ethanol, propanol or the like under an acidic condition to convert it to bisiminoalkylether. Preferable acidic substance is hydrogen chloride, where bisiminoalkylether dihydrochloride is once formed. The foregoing reaction can be also carried out in the presence of a basic catalyst such as a tertiary amine, an alkali metal alkoxide or the like. Though the reaction can proceed without a reaction solvent, it is preferable to use such a solvent as diethyl ether, etc. In any case, it is preferable to conduct the reaction under substantially water-free conditions. When the bisiminoalkylether is once obtained in the form of hydrochloride salt, etc., the hydrochloride salt is made to react with sodium hydrogen carbonate in the presence of diethyl ether and water, whereby free bisiminoalkylether of 2,2-bis(4-carboxyphenyl)hexafluoropropane having the following formula [III'] can be obtained:

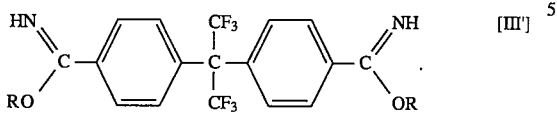

(4) The thus obtained 2,2-bis(4-carboxyphenyl)hexafluoropropane bisiminoalkylether is made to react with hydrazine, whereby the desired bisamidrazone of bis(4-carboxyphenyl)hexafluoropropane having the following formula [I'] can be obtained:

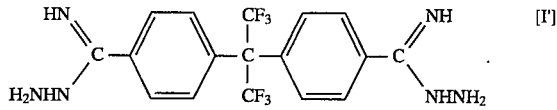

The reaction is carried out in a solvent such as methanol, ethanol, propanol, monoglyme, diglyme, triglyme, tetrahydrofuran, dioxane or the like, at a temperature of about 50° to about 150° C. in generally.

Bisamidrazone compound produced through a series of the foregoing steps can be used as a vulcanizing agent for fluorine-containing elastomer having cyano groups as cross-linkable groups. Such a fluorine-containing elastomer is a generally terpolymer comprising about 45 to about 75% by mole of tetrafluoroethylene, about 50 to about 25% by mole of perfluoro(lower alkyl vinyl ether) or perfluoro(lower alkoxy-lower alkyl vinyl ether) and about 0.1 to about 5% by mole of perfluoro unsaturated nitrile compound, the sum total of the monomers being 100% by mole.

As the perfluoro(lower alkyl vinyl ether), perfluoro(methyl vinyl ether) is usually used. As the perfluoro(lower alkoxy-lower alkyl vinyl ether), the following compounds are used:

| | |
|---|---|
| $CF_2=CFOCF_2CF(CF_3)OC_nF_{2n+1}$ | (n: 1~5) |
| $CF_2=CFO(CF_2)_3OC_nF_{2n+1}$ | (n: 1~5) |
| $CF_2=CFOCF_2CF(CF_3)O(CF_2O)_mC_nF_{2n+1}$ | (n: 1~5 and m: 1~3) |
| $CF_2=CFO(CF_2)_2OC_nF_{2n+1}$ | (n: 1~5) |

Among them, compounds whose $C_nF_{2n+1}$ group is a $CF_3$ group are preferably used.

As the perfluoro unsaturated nitrile compound as a cross-linkable side monomer, the following compounds can be used:

| | |
|---|---|
| $CF_2=CFO(CF_2)nOCF(CF_3)CN$ | (n: 2~5) |
| $CF_2=CF[OCF_2CF(CF_3)]nO(CF_2)mCN$ | (n: 1~2, m: 1~6) |
| $CF_2=CFO(CF_2)nCN$ | (n: 1~8) |
| $CF_2=CF[OCF_2CF(CF_3)]nOCF_2CF(CF_3)CN$ | (n: 1~2) |

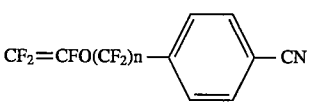
(n: 1~6)

The terpolymer comprising the foregoing components as essential ones can be further copolymerized with various fluoroolefins or vinyl compounds in such a degree as not to inhibit the copolymerization reaction and deteriorate physical properties of vulcanized products, for example, not more than about 20% by mole on the basis of the terpolymer. Fluoro-olefins for use in the present invention include, for example, vinylidene fluoride, monofluoroethylene, trifluoroethylene, trifluoropropylene, pentafluoropropylene, hexafluoropropylene, hexafluoroisobutylene, chlorotrifluoroethylene, dichlorodifluoroethylene, etc. Vinyl compounds for use in the present invention include, for example, ethylene, propylene, 1-butene, isobutylene, methyl vinyl ether, ethyl vinyl ether, butyl vinyl ether, cyclohexyl vinyl ether, vinyl acetate, vinyl propionate, vinyl chloride, vinylidene chloride, trifluorostyrene, etc.

About 0.1 to about 5 parts by weight, preferably about 0.5 to about 2 parts by weight, of bisamidrazone compound as a cross-linking agent represented by the foregoing general formula is added to 100 parts by weight of the terpolymer.

The fluorine-containing elastomer composition comprising the above-mentioned components as essential ones can further contain an inorganic filler such as carbon black, silica, etc., an acid acceptor such as oxide, hydroxide or stearate of a divalent metal, litharge, etc., and other additives, as desired. The composition can be prepared by kneading in rolls, kneader, Bambury mixer, etc. Cross-linking of the composition is carried out by heating at about 100 to about 250% for about 1 to about 120 minutes. Secondary vulcanization, when desired, is preferably carried out at about 150° to about 280° C. for not more than about 30 hours in an inert atmosphere such as a nitrogen atmosphere.

According to the present invention, there is provided a novel bisamidrazone compound, which is applicable as a vulcanizing agent for fluorine-containing elastomer having cyano groups as cross-linkable groups. Vulcanization products having a satisfactory compression set can be obtained thereby.

PREFERRED EMBODIMENTS OF THE INVENTION

The present invention will be explained in detail below, referring to Examples.

EXAMPLE 1

(1) Synthesis of 2,2-bis(4-carboxyphenyl)hexafluoropropane diamide:

105 g of 2,2-bis(4-carboxyphenyl)hexafluoropropane (purity: 92%) was charged into a 4-neck flask provided with a stirrer, a reflex tube, a dropping funnel and a thermometer, and then a mixture of 1 ml of pyridine and 160 ml of thionyl chloride was added thereto through the dropping funnel. Reaction was carried out at 60° C. for 2 hours and further at 80° C. for 3 hours with continuous stirring, and then the flask was cooled down to room temperature. The reaction mixture was filtered and unreacted thionyl chloride was distilled off from the filtrate under reduced pressure, whereby 2,2-bis(4-chlorocarbonylphenyl) hexafluoropropane was obtained as a solid.

The thus obtained 2,2-bis(4-chlorocarbonylphenyl) hexafluoropropane was added to a reactor charged with a mixture of 200 ml of aqua ammonia and 100 ml of acetonitrile, while keeping the temperature below 50° C., and stirred for further 3 hours. Then, the reaction mixture was poured into 600 ml of water and the resulting precipitates were recovered by filtration, washed with water and dried successively in desiccators previded with calcium chloride and phosphorus pentaoxide, respectively, as desiccants under reduced pressure, whereby 89 g of 2,2-bis(4-carboxyphenyl)hexafluoropropane diamide was obtained (yield: 85%).

(2) Synthesis of 2,2-bis(4-cyanophenyl)hexafluoropropane:

50 ml of thionyl chloride was dropwise added to 420 ml of dimethyl formamide obtained by distillation over calcium hydride, while keeping the temperature at 10° C. with stirring, and then heated to 35° C. under a nitrogen gas stream. Then, 67.0 g of the above-mentioned 2,2-bis(4-carboxyphenyl)hexafluoropropane diamide was slowly added thereto while keeping the reaction mixture below 50° C., and stirred for further 4 hours at 40° C. Then, the reaction mixture was poured into 1 liter of water and the resulting precipitates were recovered by filtration, washed with water, dried in a desiccator provided with phosphorus pentaoxide under reduced pressure and washed with n-hexane, whereby 59.0 g of 2,2-bis(4-cyanophenyl)hexafluoropropane having a melting point of 128° to 130° C. was obtained (yield: 85%).

Infrared absorption spectrum (KBr): 2255 cm$^{-1}$ (CN)
Elemental analysis: Calculated; C 57.63%, H 2.27%, N 7.90%, F 32.17% Found ; C 57.51%, H 2.32%, N 7.83%, F 32.01%

$^1$H-NMR (CD$_3$COCD$_3$):8.1(m), 7.65(m)
$^{19}$F-NMR (CD$_3$COCD$_3$; CF$_3$COOH base): −14.7 ppm (s, 6F)

Mass spectrum (m/z): 354(M$^+$, relative intensity 85%) 335(M$^+$—F, relative intensity 5%) 285(M$^+$—CF$_3$, relative intensity 100%)

(3) Synthesis of bisiminoethylether of 2,2-bis(4-carboxyphenyl)hexafluoropropane:

A dry hydrogen chloride gas was passed through a solution mixture of 90 ml of anhydrous ethanol, 350 ml of anhydrous diethyl ether and 83 g of 2,2-bis(4-cyanophenyl)hexafluoropropane below 15° C. up to saturation. 12 hours thereafter, the resulting crystals were recovered by filtration, washed with ether and dried, whereby 91 g of bisiminoethylether.dihydrochloride salt of 2,2-bis(4-carboxyphenyl)hexafluoropropane having a melting point of 130° to 140° C. was obtained (yield:74%).

Elemental analysis: Calculated; C 48.56%, H 4.27%, N 5.39%, F 21.95%, Cl 13.65% Found ; C 48.38%, H 4.07%, N 5.19%, F 21.99%, Cl 13.53%

$^{19}$F-NMR (CD$_3$COCD$_3$; CF$_3$COOH base): −14.65 ppm(s, 6F).

111 g of bisiminoethylether.dihydrochloride salt of 2,2-bis(4-carboxyphenyl)hexafluoropropane was added little by little to a solution of 1 liter of distilled water, 75 g of sodium hydrogen carbonate and 550 ml of diethyl ether. At 30 minutes after the end of addition, a diethyl ether layer was recovered by decantation, dried over magnesium sulfate and filtered. Diethyl ether was distilled off from the filtrate, whereby bisiminoethylether of 2,2-bis(4-carboxyphenyl) hexafluoropropane having a melting point of 88° to 90° C. was obtained.

Elemental analysis: Calculated; C 48.80%, H 3.85%, N 20.09%, F 27.25% Found ; C 48.47%, H 3.93%, N 19.16%, F 27.40%

(4) Synthesis of bisamidrazone of 2,2-bis(4-carboxyphenyl)hexafluoropropane:

The thus obtained bisiminoethylether of 2,2-bis(4-carboxyphenyl)hexafluoropropane was dissolved in a solution of 400 ml of anhydrous ethanol and 370 ml of hydrazine.monohydrate and boiled in a nitrogen gas stream for 15 minutes. After cooling, the reaction mixture was poured into 1 liter of water, and the resulting precipitates were recovered by filtration, washed with water, and dried in a desiccator provided with phosphorus pentaoxide under reduced pressure, whereby 90 g of bisimidrazone of 2,2-bis(4-carboxyphenyl)hexafluoropropane having a melting point above 300° C. was obtained (yield: 95%).

Elemental analysis: Calculated; C 56.05%, H 4.51%, N 6.27%, F 25.53% Found ; C 56.56%, H 4.39%, N 6.36%, F 25.50%

$^1$H-NMR (CD$_3$COCD$_3$): 8.1(m), 7.45(m), 6.25(br, s)
$^{19}$F-NMR (CD$_3$ COCD$_3$; CF$_3$COOH base): −14.7 ppm (s, 6F)

Mass spectrum (m/z): 418 (M$^+$).

EXAMPLE 2

After replacement of the inside gas in an autoclave having a net capacity of 1 liter with argon, 440 g of distilled water, 1.1 g of ammonium persulfate, 4.6 g of potassium dihydrogen phosphate, 4.4 g of a mixture of ammonium perfluorooctanoate—ammonium perfluorodecanoate in a ratio of 60:40 by weight and 0.3 g of sodium sulfite were charged into the autoclave. Then, a monomer mixture of 17.8 g of perfluoro(2-methyl-3,7-dioxa-8-nonenonitrile) [FCV-82], 136.7 g of perfluoro(methyl vinyl ether) [FMVE] and 63.5 g of tetrafluoroethylene [TFE] in a molar ratio of 3:54:43 was charged into the autoclave until the inside pressure of the autoclave reached 6 to 7 kgf/cm$^2$G. Then, the autoclave was heated to 60° C. and the above-mentioned monomer mixture was further charged into the autoclave until the inside pressure of the autoclave reached 11 kgf/cm$^2$G.

While keeping the polymerization temperature at 60° C., the monomer mixture was further charged intermittently into the autoclave so as to maintain the polymerization pressure at 10 to 11 kgf/cm$^2$G. Then, the reaction was continued at that polymerization temperature for further 23 hours and the inside pressure was decreased to 3.6 kgf/cm$^2$G from 11 kgf/cm$^2$G. At this point, unreacted monomer mixture was discharged from the autoclave, and the reaction mixture was freezed and solidified to precipitate the copolymer. The precipitated copolymer was washed with hot water and then with ethanol and dried at 60° C. under reduced pressure, whereby 169.8 g of white terpolymer (intrinsic viscosity ηsp/c=0.80) having the following polymer composition by $^{13}$F-NMR was obtained:

| | |
|---|---|
| FCV-82 | 2.8 mol. % |
| FMVE | 39.6 mol. % |
| TFE | 57.3 mol. % |

100 parts by weight of the thus obtained terpolymer was admixed with 15 parts by weight of MT carbon black and 2.5 parts by weight of 2,2-bis(4-carboxyphenyl)hexafluoropropane bisamidrazone obtained in Example 1, and kneaded in a roll mill. The resulting kneaded mixture was subjected to primary (press) vulcanization at 180° C. for 30 minutes and then to secondary (oven) vulcanization at 250° C. for 24 hours. The thus obtained vulcanized product had the following normal state physical properties (measured according to JIS K-6301) and compression set (P-24 O ring, measured according to ASTM Method B):

Normal state physical properties:

100% modulus 37 kg/cm$^2$

Tensile strength 105 kg/cm$^2$

Elongation 200%

Compression set

250° C. for 70 hours: 30%

275° C. for 70 hours: 37%

COMPARATIVE EXAMPLE

In Example 2, FCV-82 was replaced with the same amount of the following compound:

$CF_2=CFOCF_2CF(CF_3)O(CF_2)_2CN$ [FCV-80]

196.3 g of white terpolymer (intrinsic viscosity $\eta sp/c=$ 0.44) having the following polymer composition determined by $^{13}$F-NMR was obtained thereby:

| | |
|---|---|
| FCV-80 | 3.1 mol. % |
| FMVE | 39.6 mol. % |
| TFE | 57.3 mol. % |

100 parts by weight of the thus obtained terpolymer was admixed with 15 parts by weight of MT carbon black and 1 part by weight of bis(aminophenol)AF and kneaded in a roll mill. The resulting kneaded mixture was subjected to primary (press) vulcanization at 180° C. for 30 minutes and then to secondary (oven) vulcanization at 250° C. for 24 hours. The thus obtained vulcanized product had the following normal state physical properties and compression set, determined in the same manner as in Example 2:

Normal state physical properties:
100% modulus 34 kg/cm$^2$
Tensile strength 114 kg/cm$^2$
Elongation 230%
Compression set
275° C. for 70 hours: 60%

What is claimed is:

1. A curable, fluorine-containing elastomer composition which comprises a fluorine-containing elastomer having cyano groups as cross-linkable groups and a bisamidrazone compound represented by the following general formula: wherein R is an alkylidene group having 1 to 6 carbon atoms or a perfluoroalkylidene group having 1 to 10 carbon atoms.

2. A curable, fluorine-containing elastomer composition according to claim 1, wherein the fluorine-containing elastomer having cyano groups is a terpolymer of tetrafluoroethylene, perfluoro(lower alkyl vinyl ether) or perfluoro (lower alkoxy-lower alkyl vinyl ether) and perfluoro unsaturated nitrile compound.

* * * * *